(12) United States Patent
Lei et al.

(10) Patent No.: US 10,806,613 B2
(45) Date of Patent: Oct. 20, 2020

(54) STENT AND SECURELY-INSTALLED ARTIFICIAL VALVE REPLACEMENT DEVICE HAVING SAME

(71) Applicant: Venus Medtech (Hangzhou) Inc., Hangzhou, Zhejiang (CN)

(72) Inventors: Rongjun Lei, Hangzhou (CN); Zhifei Zhang, Hangzhou (CN); Qiming Zhang, Hangzhou (CN)

(73) Assignee: Venus medtech (Hangzhou) Inc., Hangzhou (CN)

( * ) Notice: Subject to any disclaimer, the term of this patent is extended or adjusted under 35 U.S.C. 154(b) by 6 days.

(21) Appl. No.: 16/158,597

(22) Filed: Oct. 12, 2018

(65) Prior Publication Data

US 2019/0038440 A1    Feb. 7, 2019

Related U.S. Application Data

(63) Continuation of application No. 14/856,872, filed on Sep. 17, 2015, now Pat. No. 10,098,763, which is a
(Continued)

(51) Int. Cl.
*A61F 2/89* (2013.01)
*A61F 2/90* (2013.01)
(Continued)

(52) U.S. Cl.
CPC .............. *A61F 2/90* (2013.01); *A61F 2/2418* (2013.01); *A61F 2/2436* (2013.01); *A61F 2/962* (2013.01); *A61F 2/966* (2013.01); *A61F 2/24* (2013.01); *A61F 2/82* (2013.01); *A61F 2/89* (2013.01); *A61F 2/91* (2013.01); *A61F 2/95* (2013.01); *A61F 2/9522* (2020.05); *A61F 2002/91525* (2013.01); *A61F 2002/91575* (2013.01); *A61F 2002/9505* (2013.01); *A61F 2002/9665* (2013.01); *A61F 2210/0014* (2013.01); *A61F 2220/0008* (2013.01); *A61F 2220/0025* (2013.01); *A61F 2220/0033* (2013.01);
(Continued)

(58) Field of Classification Search
CPC ............ A61F 2/2436; A61F 2002/9505; A61F 2002/9522; A61F 2002/9662; A61F 2230/0052; A61F 2250/0036
See application file for complete search history.

(56) References Cited

U.S. PATENT DOCUMENTS 8,568,469 B1 * 10/2013 Gale ........................ A61F 2/82
                                                           623/1.12
2010/0217382 A1 * 8/2010 Chau ..................... A61F 2/2418
                                                           623/1.26
(Continued)

*Primary Examiner* — Rebecca S Preston
(74) *Attorney, Agent, or Firm* — Raymond Sun

(57) ABSTRACT

A stent and a securely-installed artificial valve replacement device having the same, the stent being of a cylindrical structure; the top of the stent is provided with a fixed ear (60); the fixed ear (60) has a neck portion (601) connected to the top of the stent, and a head portion (602) engaged with the fixed head of the stent; the head portion (602) has a bending structure for improving the overall radial thickness; and the artificial valve replacement device is comprised of a stent and a prosthetic valve fixed on the stent. The stent with a bending structure overcomes the problem of easily disengaging from the fixed head of the stent, while not affecting the release of the stent.

8 Claims, 6 Drawing Sheets

Related U.S. Application Data continuation of application No. PCT/CN2014/073519, filed on Mar. 17, 2014.

(51) Int. Cl.
| | | |
|---|---|---|
| *A61F 2/24* | (2006.01) | |
| *A61F 2/962* | (2013.01) | |
| *A61F 2/966* | (2013.01) | |
| A61F 2/95 | (2013.01) | |
| A61F 2/82 | (2013.01) | |
| A61F 2/91 | (2013.01) | |
| A61F 2/915 | (2013.01) | |

(52) U.S. Cl.
CPC ........... *A61F 2230/0006* (2013.01); *A61F 2230/0019* (2013.01); *A61F 2230/0021* (2013.01); *A61F 2230/0052* (2013.01); *A61F 2230/0069* (2013.01); *A61F 2250/0036* (2013.01); *A61F 2250/0037* (2013.01); *A61F 2250/0039* (2013.01); *A61F 2250/0052* (2013.01)

(56) References Cited

U.S. PATENT DOCUMENTS

| | | | | |
|---|---|---|---|---|
| 2014/0135907 A1* | 5/2014 | Gallagher | ............... | A61F 2/95 623/2.11 |
| 2015/0173897 A1* | 6/2015 | Raanani | ............... | A61F 2/2418 623/2.11 |
| 2015/0216661 A1* | 8/2015 | Hacohen | ............... | A61F 2/2418 623/2.37 |
| 2016/0030171 A1* | 2/2016 | Quijano | ............... | A61F 2/2436 623/1.12 |

\* cited by examiner

STENT AND SECURELY-INSTALLED ARTIFICIAL VALVE REPLACEMENT DEVICE HAVING SAME

FIELD OF THE INVENTION

The present application relates to the technical field of medical apparatuses, and more particularly to a stent and a securely-installed artificial valve replacement device having same.

BACKGROUND OF THE INVENTION

When a patient's own heart valves (the mitral valve, the tricuspid valve, the aortic valve, or the pulmonary valve) mutate due to congenital or acquired diseases and hence the valves are unable to open and close normally, health and even life may be adversely affected. The mutations of the heart valves include opening incompletely and closing incompletely, both the two situations may result in increase of cardiac load, and whether the heart can normally work under the increasing load is a main basis that determines whether the human body heart valves need to be replaced.

Implantation of artificial heart valves by interventional operations causes small traumas to human bodies and has a low invasion degree, and thus it is applied more and more widely. This operation can form a small incision with a diameter of several millimeters on the skin of a patient on the premise of no use of scalpel, through the incision the vasculature system of a human body can be accessed and a transport channel can be established, and an artificial heart valve (i.e., a stent) can be transported by a special transport system to the heart and replace a defective human body valve.

An artificial heart valve replacement device in the prior art generally includes a mesh stent made of memory metal material and a clover-shaped valve that is sewed in the stent and can be opened unidirectionally, referring to FIG. 1, the stent includes three parts, which are an aortic stent 1, a valve stent 2, and a right ventricular inflow tract stent 3, and at least one T-shaped fixed ear 10 is arranged at a top edge of the stent.

In an operation, an artificial valve replacement device is transported to an implantation point by a transport system. The transport system fixes the artificial valve replacement device on a stent fixing head, a front end of the stent fixing head is provided with a streamline guiding head, a core tube extends through the stent fixing head and is connected with the guiding head, and the core tube, the stent fixing head, and the guiding head cooperatively form a sheath core. When implanting the artificial valve, the artificial valve replacement device is positioned to engage with the stent fixing head of the transport system, a sheath tube is sheathed on the outside of the sheath core, and the stent is kept in a compressed status; the sheath tube and the sheath core carrying the artificial valve replacement device is transported from an inlet of a blood vessel to a location of a diseased valve, and the artificial valve replacement device is then released; the stent will expand under the action of the body temperature and push leaves of the artificial valve towards the wall of the blood vessel to complete the positioning, afterwards, the sheath tube and the sheath core are drawn out Before the artificial valve replacement device is released, it must be mounted in the transport system stably. If the artificial valve replacement device is accidentally released, the life safety of the patient will be seriously threatened.

In the transport system, the artificial valve replacement device is fixedly mounted on the stent fixing head. FIG. 2 shows a structure of a conventional stent fixing head, wherein an outer wall of the stent fixing head defines a positioning groove 11. When mounting the artificial valve replacement device, the fixed ear 10 of the stent of the artificial valve replacement device is fittingly embedded in the positioning groove 11. In the prior art, a thickness of the fixed ear of the stent is generally about 0.4 mm, correspondingly, a depth of the positioning groove is also about 0.4 mm, that is, the depth is very small. Since there is a clearance with a width of about 0.1-0.2 mm between the stent fixing head and the inner wall of the sheath tube, and the transport system needs to pass the tortuous and complex vasculature system to transport the artificial valve replacement device to the implantation point, when the transport system turns, the sheath tube is bent and deformed, and thus the stent fixed ear is prone to slide out along the clearance, resulting in disengagement of the artificial valve replacement device.

Furthermore, in order to guide the fixed ear of the stent to enter the positioning groove successfully and facilitate the release of the artificial valve replacement device in the operating process, as shown in FIG. 3, an opening part of the positioning groove is provided with a chamfer 12, and a peripheral edge of the positioning groove is also provided with a chamfer 13, however, the chamfers are easier to cause disengagement of the artificial valve replacement device.

When not being used, the stent of the artificial valve replacement device is in a folded state, and is a compact tubular structure fabricated by machining memory metal or shape memory alloy using laser cutting. After the stent expands in a human body, it will be in tight contact with a blood vessel wall. If a thickness of the stent increases, not only does the processing difficulty increase, but also the compliance and expanding performance of the stent are affected.

SUMMARY OF THE INVENTION

The present application provides a stent, which can be stably mounted on a transport system and does not affect the normal use of the stent.

A stent, wherein the stent is a cylindrical structure, a top edge of the stent is provided with at least one fixed ear, each fixed ear includes a neck portion connected to the top edge of the stent and a head portion engaging with a stent fixing head, and the head portion is provided with a bent structure configured for increasing an overall radial thickness of the stent.

If not specially described, the term "radial direction" of the present application refers to a radial direction of the stent. Since the stent is a cylindrical structure, the radial thickness refers to a thickness of the head portion along a radial direction of the stent.

The whole head portion or a part of the head portion can be the bent structure. After adopting the bent structure, an overall thickness of the head portion will increase; preferably, a ratio of a radial thickness of the bent structure to a radial thickness of the neck portion is 1.2~3:1.

A radial thickness of the neck portion can be regarded as an overall thickness of a fixed ear without any bent structure in the prior art. When the head portion is bent, compared with the neck portion, its thickness increases and can provide an anti-disengagement function.

An outer wall of the stent fixing head is provided with a positioning groove, when mounting the stent, the head portion of the fixed ear engages within the positioning groove, and the outside of the stent is surrounded by the sheath tube of the stent. A clearance fit is formed between the sheath tube of the stent and the stent fixing head; if the clearance is too large (e.g., large than 0.1 mm), since the sheath tube of the stent is made of thin-walled polymer material, when it is subjected to a radial compression force from the head portion of the fixed ear, it will generate a flexible deformation, such that the clearance between the sheath tube of the stent and the stent fixing head will increase several times at a part of the stent fixing head contacting the fixed ear, thereby resulting in that the fixed ear disengages from the positioning groove; on the contrary, if the clearance is too small, it will be caused that an excessive axial resistance is generated when the stent is carried and released, thereby resulting in operating difficulty of the operation. Therefore, the requirement for the matching accuracy between the stent fixing head and the sheath tube of the stent has become a main problem in the prior art. The present application adopts the bent structure of the head portion of the fixed ear to increase the radial thickness of the head portion, so that the radial thickness of the head portion equals several times of the width of the clearance. Therefore, the requirement for the accuracy of the clearance can be significantly reduced, and it can be reliably ensured that the stent fixed ear will not separate from the stent fixing head even though the axial resistance is not increased, so that the stent can be stably mounted in the transport system.

Furthermore, the bent structure is formed by re-machining the stent at which laser engraving has been completed, and thus does not affect biological performance of the stent.

There are many types of bent structures. When the whole head portion is a bent structure, as one choice, the head portion is substantially arc-shaped, and a concave portion of the arc shape is positioned towards an axis of the stent.

Here, a thickness of the head portion refers to a difference between a radial height of a middle portion of the arc shape and a radial height of either end of the arc shape.

As another choice, the head portion is substantially wave-shaped.

Here, a thickness of the head portion refers to a difference between a radial height of any wave peak and a radial height of any wave trough.

The wave-shaped head portion should have at least two wave peaks.

Preferably, the wave peaks and the wave troughs of the wave-shaped head portion are alternately arranged along a circumference of the stent.

In order to embed the fixed ear in the positioning groove of the stent fixing head more stably, two ends of the head portion that abut a bottom of the positioning groove are wave troughs of the head portion.

When a part of the head portion is a bent structure, as a choice, two side edges of the head portion are bent towards each other.

When being bent, two side edges of the head portion can be bent towards the same side, and can also be bent towards two opposite sides respectively.

A bent angle of each of the two side edges is usually at 160-180 degrees, and preferably, at 180 degrees. When the bent angles of the two side edges are at 180 degrees, a radial thickness of the fixed ear equals two times of a radial thickness of the fixed ear before being bent.

As another choice, a top edge of the head portion is bent towards the neck portion.

A bent angle of the top edge is usually at 160-180 degrees, and preferably, at 180 degrees. When the bent angle is at 180 degrees, a radial thickness of the bent fixed ear equals two times of a radial thickness of the fixed ear before being bent.

In order to facilitate the machining of the bent structures, preferably, the fixed ear is T-shaped, and a top end of the neck portion of the fixed ear is connected with a center of a bottom of the head portion.

There can be a plurality of fixed ears arranged on a top edge of the stent evenly. Preferably, the number of the fixed ears is 2~4.

Preferably, the projection locations of the top edges of the plurality of fixed ears on an axis of the stent are arranged to be staggered. That is, heights of the top edges of the plurality of fixed ears are different, and in particular, heights of the top edges of every two fixed ears differ from each other. Therefore, when the stent is fixed onto the transport system, the plurality of fixed ears can be positioned sequentially; for example, a fixed ear having the highest top edge can be positioned at first, and all other fixed ears can be positioned sequentially, wherein each fixed ear having a higher top edge is positioned prior to each fixed ear having a lower top edge, so that the operation is more convenient.

The present application further provides a stably-mounted artificial valve replacement device, which comprises the above-described stent and a prosthesis valve fixed on the stent.

The prosthesis valve can be a prosthesis tricuspid valve, a prosthesis pulmonary valve, a prosthesis aortic valve, and so on.

The prosthesis valve can be sewed on an inner wall of the stent, and can also be fixed by other conventional methods.

By the arrangement of the bending structure(s), the stent of the present application overcomes the problem that the stent is prone to disengage from the stent fixing head, the stent can be stably mounted on the transport system, so that the safety is higher; moreover, the release of the stent is not affected.

The stent of the present application is designed and improved on the basis of conventional stents, therefore, it is simple, convenient, and easy to operate.

DETAILED DESCRIPTION OF THE PREFERRED EMBODIMENT

The present application will be further described hereafter with reference to the accompany drawings and embodiments.

An artificial valve replacement device of the present application comprises a stent and a prosthesis valve fixed on the stent.

Taking an aortic stent as an example, a structure of the artificial valve replacement device of the present application will be described hereafter. However, it should be noted that the artificial valve replacement device of the present application is not limited to use the aortic stent, but can also use a pulmonary stent, a tricuspid valve stent, etc.

Figure 1:
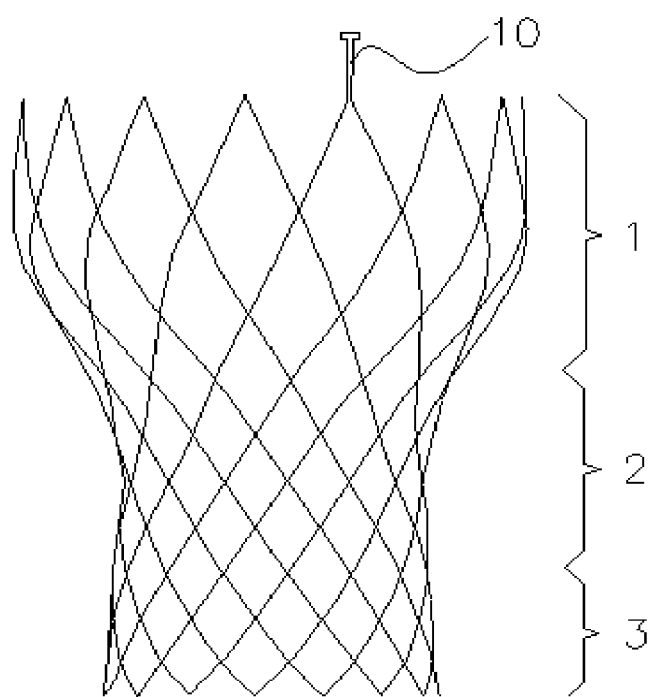
FIG. 1 is a structural schematic view of a stent of an artificial valve replacement device in the prior art.
Figure 2:
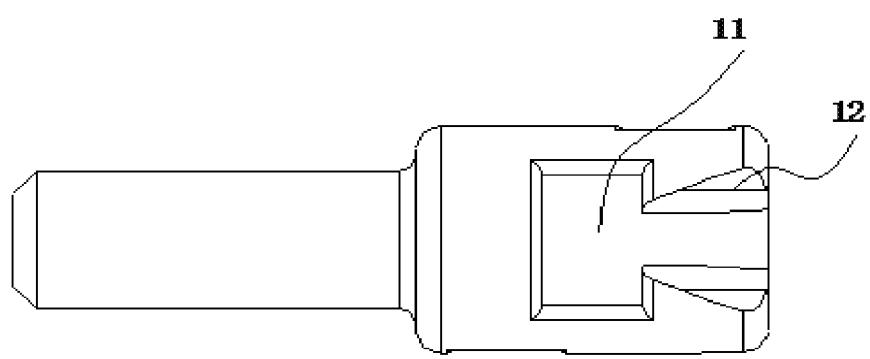
FIG. 2 is a structural schematic view of a stent fixing head in the prior art.
Figure 3:
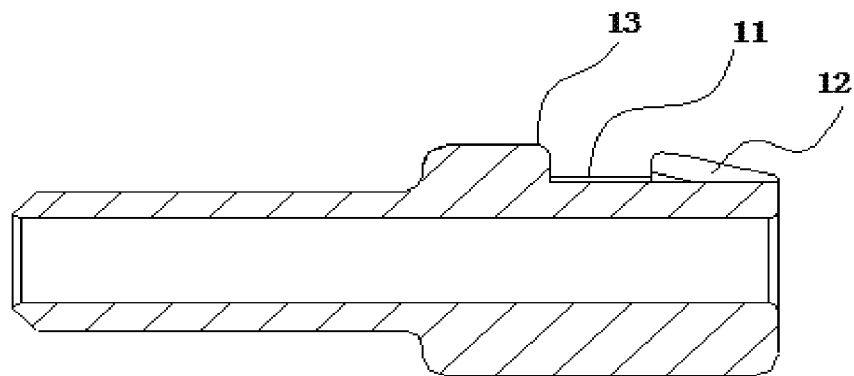
FIG. 3 is a cut-away view of the stent fixing head shown in FIG. 2.
Figure 4:
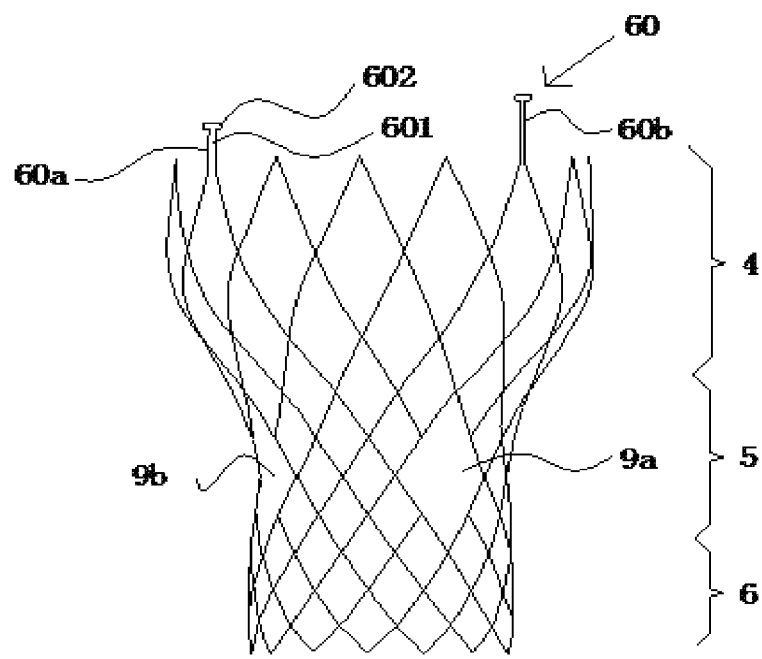
FIG. 4 is a structural schematic view of a stent of an artificial valve replacement device of the present application.

As shown in FIG. 4, the stent (aortic stent) is a netlike cylindrical structure, which comprises an aortic stent 4, a valve stent 5, and an inflow tract stent 6 that are connected sequentially.

The stent comprises a plurality of diamond unit meshes arranged continuously, and three hollow areas are arranged at a side wall of the valve stent 5. Due to the limit of the view angle, only two hollow areas 9a, 9b of the three hollow areas are visible in FIG. 4. The hollow areas are used to respectively accommodate a top end of a prosthesis valve when the prosthesis valve is opened. Each hollow area is formed by combining four adjacent diamond unit meshes together, that is, at least a part of the skeletons inside the hollow area are removed to form the hollow area. In this way, the stent is not only easy to process but also able to achieve a good overall strength.

Of course, the shapes of the mesh structures of the stent are not limited to diamond, and can also be regular or irregular oval, round, rectangular, and so on, as long as they can meet the requirement for supporting force and compliance of the stent.

A top edge of the aortic stent 4 is provided with at least one fixed ear 60, which is configured to engage within a positioning groove of a stent fixing head of a transport system when the stent is implanted into a human body.

The fixed ear 60 is substantially T-shaped, in particular, the fixed ear 60 includes a neck portion 601 and a head portion 602, the neck portion 601 is connected with the top edge of the aortic stent 4, and the head portion 602 engages with a stent fixing head; a top end of the neck portion 601 of the fixed ear 60 is connected with a center of a bottom of the head portion 602, and the head portion 602 further comprises a bent structure that increases an overall radial thickness of the head portion 602.

Figure 5:
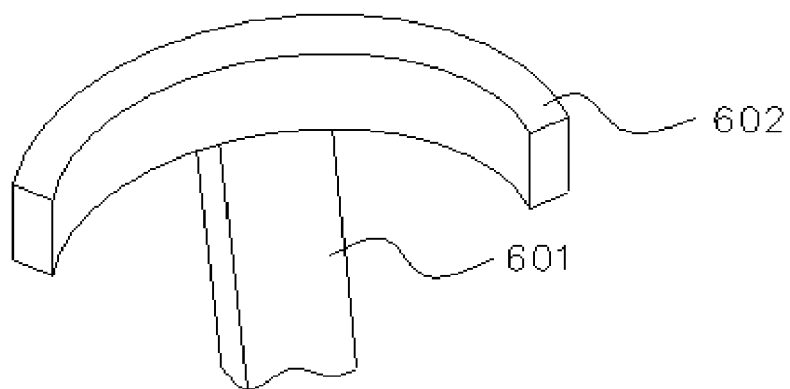
FIG. 5 is a structural schematic view of a first type of fixed ear of FIG. 4.
Figure 6:
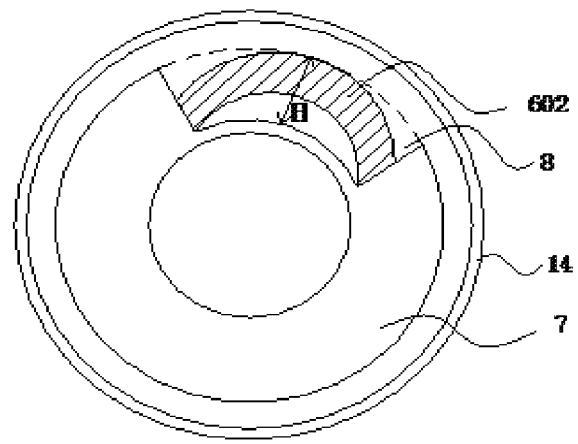
FIG. 6 is a schematic view of mounting the fixed ear shown in FIG. 5 onto a transport system (according to a first fitting method)
Figure 7:
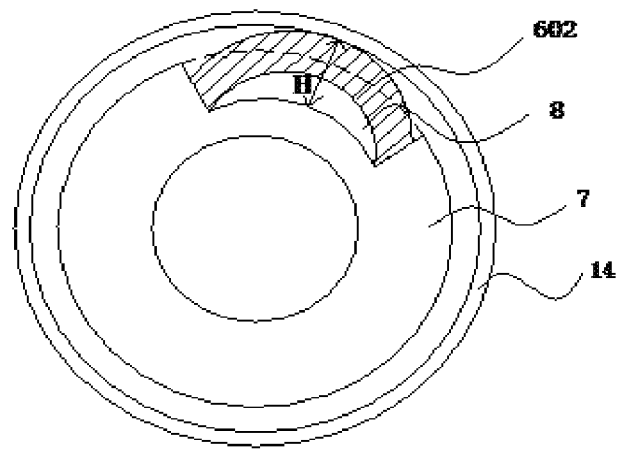
FIG. 7 is a schematic view of mounting the fixed ear shown in FIG. 5 onto a transport system (according to a second fitting method)

FIG. 5 illustrates a first embodiment of the bent structure of the head portion 602 of the fixed ear 60 of the present application. In this embodiment, the whole head portion 602 of the fixed ear is bent to be arc-shaped, and a concave portion of the arc shape is positioned towards an axis of the stent. In this way, an overall radial thickness H of the head portion 602 (i.e., a difference between a height of a middle portion of the arc shape and a height of either end of the arc shape) is increased. When the fixed ear 60 engages with a positioning groove, as shown in FIG. 7, a depth of a positioning groove 8 of a stent fixing head 7 can be increased appropriately (however, it is also possible that the depth is not increased), so that the head portion 602 of the fixed ear 60 is in tight contact with an inner wall of a sheath tube 14. Of course, when the depth of the positioning groove 8 is increased, the depth can be fit for the thickness of the head portion 602 of the fixed ear 60, as shown in FIG. 6; in this way, even though the sheath tube 14 is bent and/or deformed, the fixed ear 60 is not prone to disengage from the positioning groove 8, and thus the stent is prevented from disengagement.

Even though the depth of the positioning groove 8 is unchanged, since the overall radial thickness of the head portion 602 is increased so that the radial thickness equals several times of a width of a clearance between the sheath tube 14 and the stent fixing head 7, requirement for the accuracy of the clearance can still be greatly reduced, and requirement for the accuracy of the sheath tube can also be reduced at an order of magnitude, such that the processing technology is simpler and easier to perform.

Figure 8:
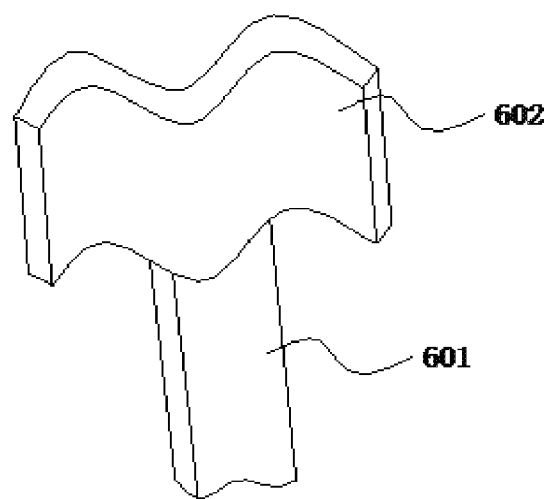
FIG. 8 is a structural schematic view of a second type of fixed ear of FIG. 4.
Figure 9:
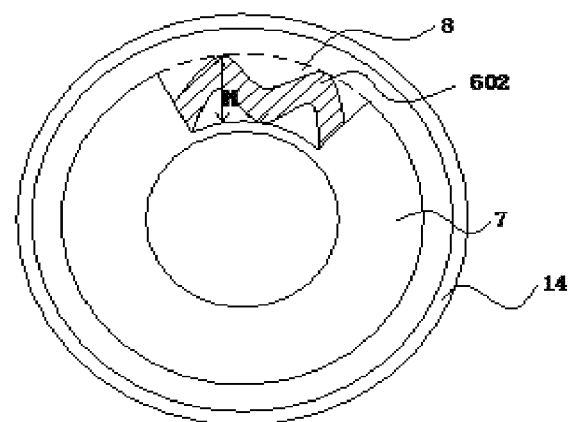
FIG. 9 is a schematic view of mounting the fixed ear shown in FIG. 8 onto a transport system (according to a first fitting method)
Figure 10:
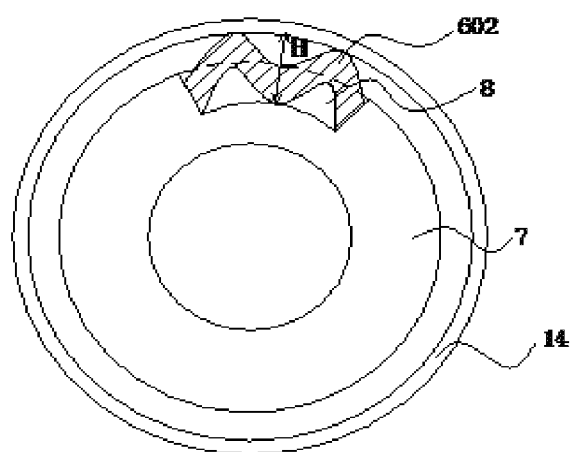
FIG. 10 is a schematic view of mounting the fixed ear shown in FIG. 8 onto a transport system (according to a second fitting method)

FIG. 8 illustrates a second embodiment of the bent structure, wherein the head portion 602 of the fixed ear 60 is substantially wave-shaped, and wave peaks and wave troughs of the wave-shaped head portion 602 are alternately arranged along a circumference of the stent. In particular, two ends of the head portion 602 that abut a bottom of the positioning groove 8 are wave troughs of the head portion 602, so that the fixed ear 60 can be embedded in the positioning groove 8 of the stent fixing head 7 more stably. FIG. 9 and FIG. 10 show mounted states of the head portion 602 of the wave-shaped fixed ear 60 in the transport system when mounting the stent.

Figure 11:
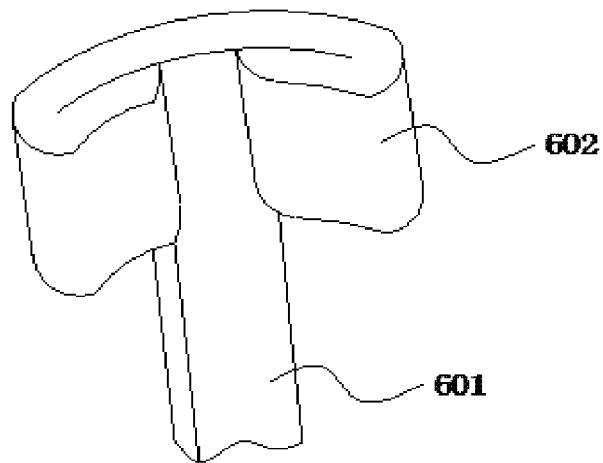
FIG. 11 is a structural schematic view of a third type of fixed ear of FIG. 4.

In a third embodiment of the bent structure of the head portion 602, the head portion 602 of the fixed ear 60 is partially bent, in particular, two side edges of the head portion 602 are bent towards each other. As shown in FIG. 11, the two side edges of the head portion 602 are bent towards the same side, the bent angle of each side edge equals 180 degrees, and a thickness of the bent fixed ear 60 equals two times of a thickness of the fixed ear 60 before being bent.

Of course, the two side edges of the head portion 602 can also be bent towards two opposite sides respectively, so that the head portion 602 is substantially S-shaped.

Figure 12:
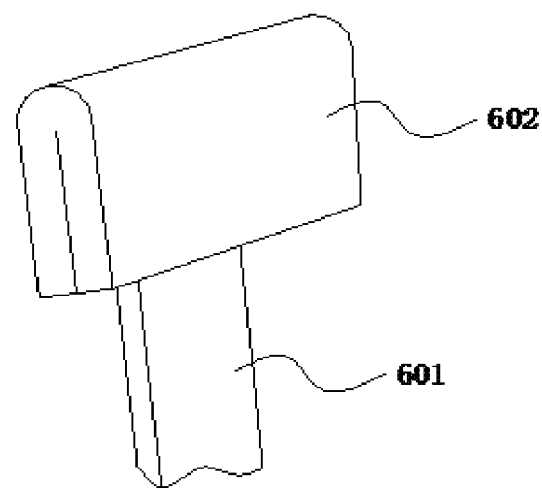
FIG. 12 is a structural schematic view of a fourth type of fixed ear of FIG. 4.

FIG. 12 illustrates a fourth embodiment of the bent structure of the head portion 602 of the present application. In this embodiment, the top edge of the head portion 602 is bent towards the neck portion 601, the bent angle equals 180 degrees, and a thickness of the bent fixed ear 60 equals two times of a thickness of the fixed ear 60 before being bent; of course, a bent angle in the range of about 160~180 degrees can also achieve good effect.

Obviously, when the fixed ear 60 shown in FIG. 11 or FIG. 12 engages with the positioning groove 8, the aforementioned engaging ways (e.g., the first engaging way) can also be adopted, and these engaging ways do not need to be repeatedly detailed here.

It should be noted that the bent structure of the head portion 602 of the fixed ear 60 of the present application is not limited to the above-described embodiments but can have many variations. For example, each of the two side edges of the head portion 602 of the fixed ear 60 shown in FIG. 11 is bent only once, actually, each of the two side edges can be bent twice or more times, so that a thickness of the bent fixed ear 60 with the multilayer laminate structure equals three or more times of a thickness of the fixed ear 60 before being bent.

Furthermore, in the bent structure, the bending or curving angle of the head portion 602 can be adjusted according to actual situations.

Figure 13:
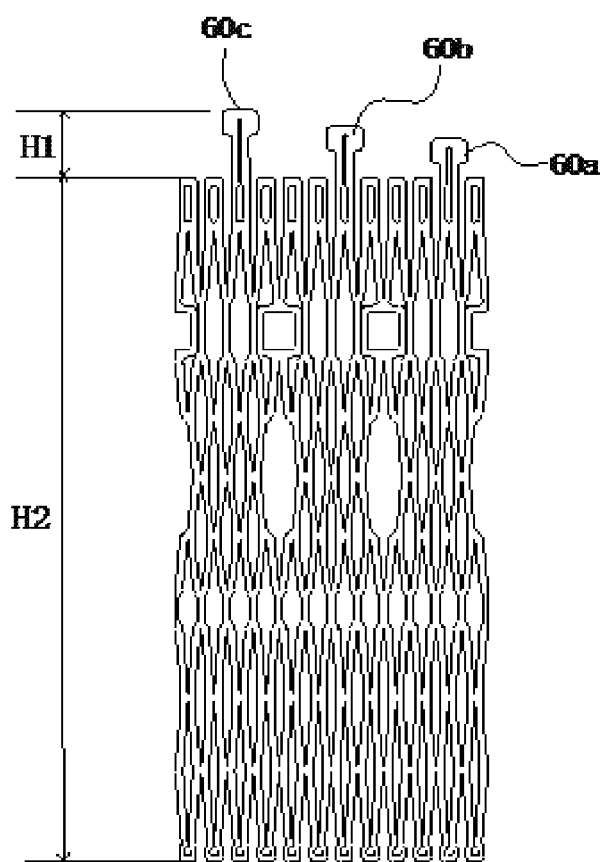
FIG. 13 is a schematic view of opening the stent of the artificial valve replacement device of the present application before the stent is released.

The number of the fixed ears 60 is usually three, as shown in FIG. 13, three fixed ears 60a, 60b, and 60c are provided. Heights of top edges of three fixed ears 60a, 60b, and 60c are different, for example, it can be seen from FIG. 13 that the fixed ear 60b is obviously higher than the fixed ear 60a, and the fixed ear 60c is obviously higher than the fixed ear 60b.

A height H1 of the fixed ear 60c is a distance between a top edge of the aortic stent 4 and the top edge of the fixed ear 60c. In this embodiment, the height of the fixed ear 60c is about 7 mm, the height of the fixed ear 60b is about 5 mm, the height of the fixed ear 60a is about 2.8 mm, and a height H2 of the stent (without the heights of the fixed ears) is about 55 mm.

It needs to be explained that the stent of the artificial valve replacement device is in a folded state when it is not used, that is, it is a compact tubular structure, and is usually fabricated by machining tubing made of memory metal material using laser cutting; while it is implanted into a human body and released, it will expand under the action of the body temperature and form a loose cylindrical structure. In the present application, if not specially described, all described structures of the artificial valve replacement device and the stent thereof refer to the structures having completely expanded in a human body.

What is claimed is:

1. A tubular foldable stent, comprising, along a longitudinal direction:
    a first section;
    a second section; and
    a valve section connected between the first section and the second section, the valve section being configured for attaching a prosthetic valve therein,
    wherein the first section has at least one fixed ear provided at one end thereof spaced-apart from the valve section, and each fixed ear is T-shaped and comprises:
        a neck portion connected to the end of the first section; and
        a head portion;
    wherein within each fixed ear, the head portion has a width greater than a width of the neck portion in a circumferential direction of the stent,
    wherein each head portion is curved in the circumferential direction; and
    wherein each head portion has two circumferential side edges bent in the circumferential direction towards each other.

2. The tubular foldable stent according to claim 1, wherein each head portion is entirely or partially curved.

3. The tubular foldable stent according to claim 1, wherein within each fixed ear, a ratio of an overall radial thickness of the head portion to a radial thickness of the neck portion is in the range of 1.2 to 3:1.

4. The tubular foldable stent according to claim 1, wherein a bent angle of each of the two side edges is in the range of 160 to 180 degrees.

5. The tubular foldable stent according to claim 1, wherein within each fixed ear, the head portion is positioned symmetrical with respect to the neck portion in the circumferential direction.

6. An artificial valve replacement device, comprising:
    a tubular foldable stent, comprising, along a longitudinal direction:
        a first section;
        a second section; and
        a valve section connected between the first section and the second section,
        wherein the first section has at least one fixed ear provided at one end thereof spaced-apart from the valve section, and each fixed ear is T-shaped and comprises:
            a neck portion connected to the end of the first section; and
            a head portion;
        wherein within each fixed ear, the head portion has a width greater than a width of the neck portion in a circumferential direction of the stent,
        wherein each head portion is curved in the circumferential direction; and
    a prosthetic valve is fixed at the valve section of the stent, and
    wherein each head portion has two circumferential side edges bent in the circumferential direction towards each other.

7. The artificial valve replacement device according to claim 6, wherein each head portion is entirely or partially curved.

8. The artificial valve replacement device according to claim 6, wherein within each fixed ear, a ratio of an overall radial thickness of the head portion to a radial thickness of the neck portion is in the range of 1.2 to 3:1.

* * * * *